United States Patent [19]

Abair et al.

[11] 4,113,809

[45] Sep. 12, 1978

[54] HAND HELD ULTRASONIC NEBULIZER

[75] Inventors: Raymond L. Abair; Stanley J. Kulish, Jr., both of Toledo, Ohio

[73] Assignee: Champion Spark Plug Company, Toledo, Ohio

[21] Appl. No.: 784,044

[22] Filed: Apr. 4, 1977

[51] Int. Cl.² .......................................... A61M 15/00
[52] U.S. Cl. .......................................... 261/81; 261/1; 261/DIG. 48; 261/DIG. 65; 128/DIG. 2; 128/194; 239/102
[58] Field of Search ...................... 261/1, 81, DIG. 48, 261/DIG. 65; 128/DIG. 2, 185–194; 239/102

[56] References Cited

U.S. PATENT DOCUMENTS

| 3,490,697 | 1/1970 | Best, Jr. | 261/DIG. 48 |
| 3,561,444 | 2/1971 | Boucher | 128/DIG. 2 |
| 3,746,000 | 7/1973 | Edwards | 261/DIG. 65 |
| 3,828,773 | 8/1974 | Buch et al. | 239/102 |
| 3,989,042 | 11/1976 | Mitsui et al. | 128/DIG. 2 |

Primary Examiner—Frank W. Lutter
Assistant Examiner—Gregory N. Clements
Attorney, Agent, or Firm—Oliver E. Todd, Jr.

[57] ABSTRACT

An improved ultrasonic nebulizer for administering a medicament aerosol to a patient. Output from an oscillator is connected through a series inductor to a transducer adjacent a reservoir which generates aerosol from the medicament. The inductor is tuned for series resonance with the bulk capacitance of the transducer. An impedance change in the transducer when liquid is removed or consumed from the reservoir reduces the power delivered to the transducer and prevents transducer damage.

7 Claims, 4 Drawing Figures

U.S. Patent  Sept. 12, 1978  4,113,809
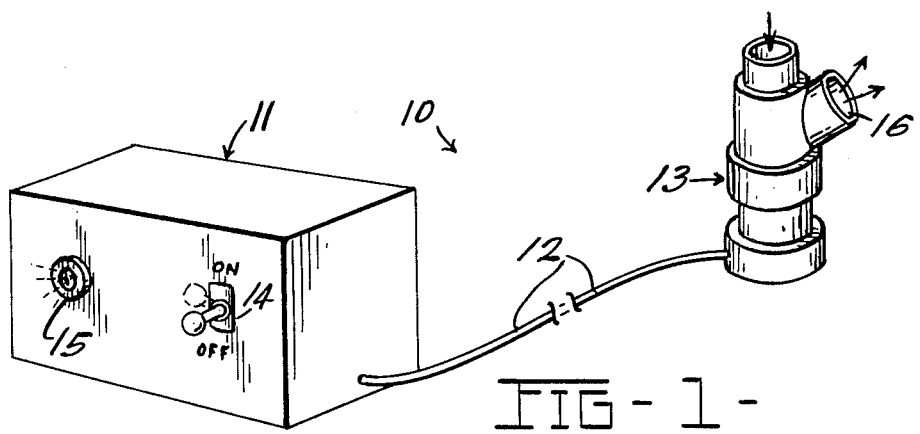
FIG-1-
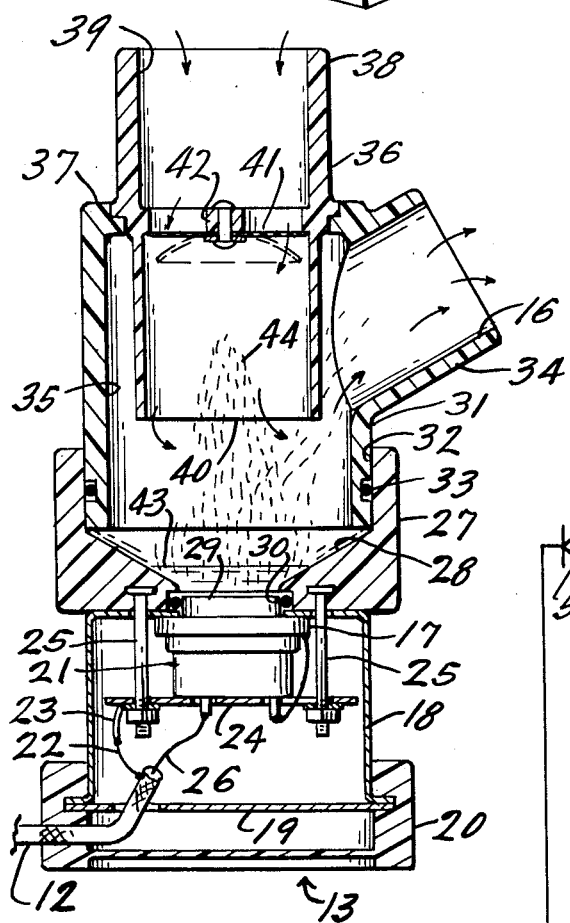
FIG-2-
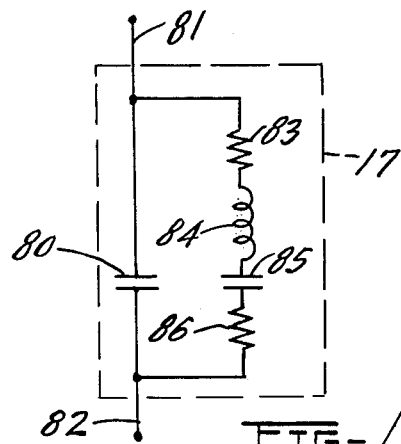
FIG-4-
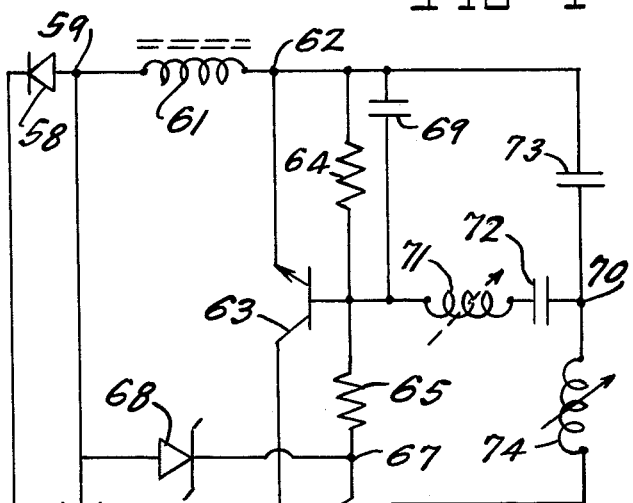
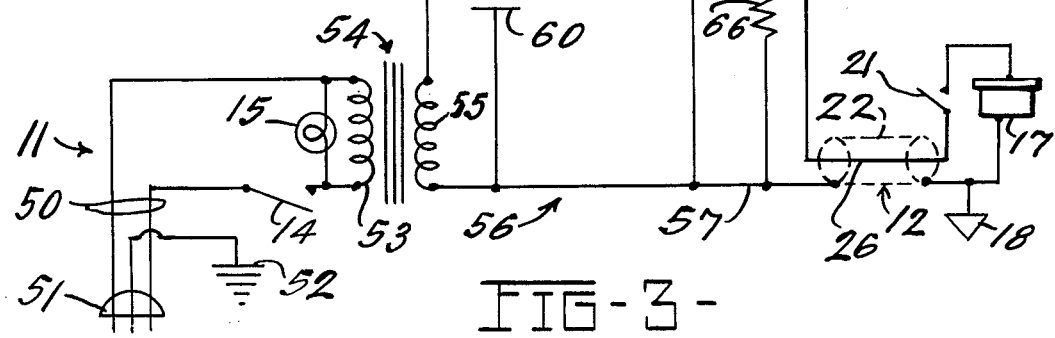
FIG-3-

HAND HELD ULTRASONIC NEBULIZER

BACKGROUND OF THE INVENTION

This invention relates to medical devices and more particularly to an improved ultrasonic nebulizer for administering a medicament aerosol to a patient.

Ultrasonic nebulizers are commonly used for administering medicament aerosols to patients suffering from respiratory diseases such as emphysema. Ultrasonic nebulizers generally comprise a ceramic piezoelectric transducer located at the bottom of a liquid reservoir and a radio frequency power supply for exciting the transducer. When the transducer is excited by alternating current having a frequency at or near the resonant frequency of the transducer, the transducer vibrates to produce a geyser above the surface of the liquid in the reservoir and extremely fine liquid particles from the geyser. Air inhaled by a patient is drawn past the geyser to entrain the fine liquid particles for delivering the medicament to the patient.

In hospitals and clinics, relatively large ultrasonic nebulizers are commonly used. These nebulizers are placed on tables or are mounted on a floor stand. For patients requiring quantitative administration of medication, smaller portable nebulizers are desirable. In one embodiment, a hand-held nebulizer is provided with an internal power supply which generates radio frequency current. A measured dose of medicament is placed in the nebulizer for administering to the patient. However, considerable problems have occurred in prior art ultrasonic nebulizers of this type. In one prior art hand-held ultrasonic nebulizer, a trigger or finger actuated switch has been provided on the nebulizer for manually energizing the transducer during inhalation. However, since an aerosol is not generated unless the switch is closed, some of the inhaled gas will not include medication if the patient does not properly time the switch closure with inhalation. In another embodiment, the power supply may be connected to continuously energize the transducer. In both types of ultrasonic nebulizers, there is a strong possibility of damaging the transducer by allowing the transducer to operate in a mechanically unloaded or dry condition. This is particularly true since it is desirable to operate the nebulizer until dry to administer an entire measured dose of medicament to the patient and also because the patient may at some point tip the hand-held nebulizer, allowing the liquid medicament to flow away from the transducer. The larger size nebulizers which are mounted on a stand or supported on a table are provided with liquid level sensing switches which shut off the nebulizers when the liquid drops below a predetermined level.

Typical prior art ultrasonic nebulizers include a radio frequency power source which is conventionally coupled to the piezoelectric crystal transducer. This arrangement delivers full power to the transducer when it is mechanically loaded or covered with a liquid and also when it is not covered with a liquid and is mechanically unloaded. If the transducer is allowed to run dry or become mechanically unloaded, it will be damaged or destroyed if power is continuously applied.

SUMMARY OF THE INVENTION

According to the present invention, the circuit for an ultrasonic nebulizer is arranged such that power to a piezoelectric crystal transducer automatically decreases when the transducer is dry or unloaded to protect the transducer from damage due to excessive power dissipation. The power decrease can be caused by providing an inductive coupling between a power oscillator and the transducer which is tuned to resonate with the bulk capacitance of the transducer. A change in impedance in the transducer when mechanical loading is removed detunes the circuit by shunting the bulk capacitance of the transducer with a low resistance which reduces power delivered to the transducer.

The nebulizer of the present invention is provided with a radio frequency power source which drives a piezoelectric crystal transducer at or near its resonant frequency. The radio frequency output from the oscillator is coupled through an inductor to the transducer. The inductor is tuned to resonance with the bulk capacitance of the transducer. When the liquid load is consumed or otherwise removed from the transducer, there is a considerable decrease in the effective resistance of the transducer which shunts the bulk capacitance of the transducer. Thus, the equivalent properties or impedance of the transducer changes from one which is primarily capacitive to one which is primarily a low resistance to signals at or near the resonant frequency of the transducer. As a result of this impedance change, the power delivered to the transducer is substantially reduced, thereby protecting the transducer from damage. In normal use the patient inhales periodically, removing aerosol and heat from the nebulizer. The nebulizer is designed to dissipate heat produced by power losses within the transducer when the patient inhales aerosol. However, if aerosol is not withdrawn periodically from the nebulizer, the heat resulting from the transducer inefficiency when it is in a mechanically loaded condition may cause the temperature of the liquid to rise objectionally over a period of time. This potential problem can be eliminated by incorporating a protective thermal switch into the system.

Since the transducer is protected from damage caused by excess power dissipation when operated in a mechanically unloaded or dry condition, the ultrasonic nebulizer can be energized continuously rather than requiring a trigger or switch as in prior art hand-held ultrasonic nebulizers. The continuously generated aerosol is collected within the nebulizer by a tubular sleeve and one-way valve, except during inhalation by a patient. As a consequence, the patient receives an immediate dose of the medicament during each inhalation. Furthermore, the patient can consume the entire measured dose of medicament placed in the nebulizer without concern of damaging the nebulizer by allowing it to run dry.

Accordingly, it is a preferred object of the invention to provide an improved ultrasonic nebulizer.

Another object of the invention is to provide an improved circuit for protecting a piezoelectric transducer from damage when the transducer is operated in a mechanically unloaded condition.

Other objects and advantages of the invention will become apparent from the following detailed description, with reference being made to the accompanying drawings.

BRIEF DESCRIPTION OF THE DRAWINGS

FIG. 1 is a perspective view of a hand-held ultrasonic nebulizer and remote power supply constructed in accordance with a preferred embodiment of the invention;

FIG. 2 is a vertical cross sectional view through the ultrasonic nebulizer of FIG. 1 constructed in accordance with the present invention;

FIG. 3 is a schematic circuit diagram of an ultrasonic nebulizer power supply constructed in accordance with the present invention; and FIG. 4 is a schematic circuit diagram of the equivalent circuit of a piezoelectric ceramic transducer for an ultrasonic nebulizer when operated at or near resonance.

DESCRIPTION OF THE PREFERRED EMBODIMENTS

Turning now to the drawings and particularly to FIG. 1, nebulizing apparatus 10 is shown in accordance with a preferred embodiment of the invention. The apparatus 10 generally comprises a power supply 11 which generates and applies a radio frequency signal over a coaxial cable 12 to a hand-held ultrasonic nebulizer 13. The power supply 11 is provided with an on/-off switch 14 and a pilot light 15. No other controls are necessary for the power supply 11 or for the ultrasonic nebulizer 13 since aerosol will be emitted from the ultrasonic nebulizer 13 only when a patient inhales through an aerosol outlet 16 and the ultrasonic nebulizer 13 is protected from damage when operated in a mechanically unloaded or empty state. Preferably, the ultrasonic nebulizer 13 is sufficiently small to permit it to be hand-held by a patient. The small size of the ultrasonic nebulizer 13 makes it particularly convenient for use in the home and for use by bedridden patients. However, in a modified embodiment of the apparatus 10 the power supply 11 and the ultrasonic nebulizer 13 may be combined into a single housing placed on a table or other suitable support. For economy in use of medication and to permit quantitative application of medication, it is desirable to have a minimum length of delivery tube between the nebulizer and the patient.

Turning now to FIG. 2, a vertical cross sectional view is shown through the ultrasonic nebulizer 13. The ultrasonic nebulizer 13 includes a piezoelectric ceramic transducer 17 mounted within a metal housing formed from a can 18 and a cover 19. The can 18 and cover 19 are held together by means of a protective end member 20 formed from rubber or a resilient synthetic resinous material. The coaxial cable 12 passes through the end member 20 and the cover 19 and is connected through a thermal switch 21 to the transducer 17. Shielding 22 on the cable 12 is connected through a ground lug 23, a plate 24 and bolts 25 to the can 18 and then to top face of the transducer 17. The shielded wire 26 in the cable 12 is connected through the thermal switch 21 to the bottom face of the transducer 17. During normal operating conditions, the thermal switch 21 maintains electrical connection from the coaxial cable 12 to the transducer 17. However, in the event that the transducer 17 exceeds a predetermined safe temperature, such as about 140° F., the thermal switch 21 opens to interrupt power to the transducer 17. Since heat is generated from within the transducer 17, the transducer 17 will reach this temperature while liquid in the nebulizer 13 is still much cooler, say 110° F.

The bolts 25 are anchored within a housing member 27 which abuts the can 18. The plate 24 and bolts 25 clamp the transducer 17, the thermal switch 21 and the can 18 together and to the housing member 27. The housing member 27 is generally cup shaped, having an interior opening or cavity 28 which forms a liquid reservoir for holding a suitable medicament for application to a patient. The opening 28 is closed at its bottom by an upper surface 29 on the transducer 17. A suitable seal, such as an O-ring 30 is positioned between the transducer 17 and the housing member 27 to prevent liquid leakage therebetween while permitting the transducer surface 29 to vibrate. A tubular sleeve 31 fits within an upper portion 32 of the opening 28. An O-ring 33 seals the interface between the sleeve 31 and the upper opening portion 32. A tubular sleeve 34 angles outwardly and upwardly from the sleeve 31 for defining the aerosol outlet 16. The aerosol outlet 16 communicates with an interior opening 35 in the sleeve 31 located above the cavity 28.

A tubular member 36 is mounted coaxially within an upper end 37 of the sleeve 31. An upper end 38 of the tubular member 36 forms an air inlet opening 39 for the ultrasonic nebulizer 13 while a lower end 40 projects downwardly into the sleeve opening 35 past the aerosol outlet 16. A check valve in the form of a resilient flap 41 is mounted within the tubular member 36 between the upper end 38 and the lower end 40. The resilient flap 41 is normally positioned to close passages 42. As air is drawn through the inlet 39 when a patient inhales at the aerosol outlet 16, the resilient flap 41 flexes to permit air passage through the tubular member 36 into the sleeve opening 35. The lower end 40 of the tubular member 36 is located coaxially within and spaced from the sleeve opening 35 and extends below the aerosol outlet 16. Prior to operating the ultrasonic nebulizer 13, a measured dose of medicament is placed in the chamber 28 to cover the transducer surface 29, as shown by the body of the liquid 43. When the transducer 17 is then energized during operation of the ultrasonic nebulizer 13, a geyser 44 forms above the surface of the liquid 43 and fine liquid particles are generated in the chamber above the body of liquid 43. The tubular member 36 prevents the liquid particles in the geyser 44 from directly entering the aerosol outlet 16. When a patient positions his mouth over the aerosol outlet 16 and inhales, air is drawn through the inlet 39 past the check valve flap 41 into the lower end 40 of the tubular member 36. At this point, liquid particles are entrained within the air and the resulting aerosol is drawn upwardly through the annular space between the lower end 40 of the tubular member 36 and the sleeve opening 35. From there, the aerosol mixture flows through the outlet 16 to the patient. If desired, a disposable or a sterilizable plastic sleeve or mouthpiece may be attached to the aerosol outlet 16 to facilitate cleaning and also to protect the patient. When the patient is not inhaling, some of the aerosol agglomerates and drops back into the body of liquid 43. Therefore, only the inhaled aerosol is consumed, even though the nebulizer 13 is continuously energized.

Turning now to FIG. 3, a schematic circuit diagram is shown for the power supply 11, the coaxial cable 12, the thermal switch 21 and the transducer 17. The power supply 11 is operated from standard commercial power sources, such as a 110 volt, 60 Hz. commercial power source in the United States and Canada or a 220 or 230 volt, 50 Hz. power source available in many other countries. The power supply 11 is connected through a standard line cord 50 and plug 51 to the commercial power source. The plug 51 is shown as having three pins, one of which is connected to a ground 52 which includes a cabinet enclosing the power supply 11. A second pin on the plug 51 is connected to one side of a primary winding 53 on a power transformer 54 while the other pin is connected through the power switch 14 to the primary winding 53. The pilot light 15 is shown as being connected in parallel with the primary winding 53 to be energized whenever the switch 14 is closed. If desired, the pilot light 15 may be omitted.

The power transformer 54 has a secondary winding 55 which powers a closely coupled radio frequency oscillator circuit 56. One side of the secondary winding 55 is connected to a positive bus 57 which is locally grounded through the coaxial cable shielding 22 to the can 18 and cover 19 which enclose the transducer 17. A second side of the secondary winding 55 is connected through a diode rectifier 58 to a negative terminal 59. A filter capacitor 60 is connected from the terminal 59 to the bus 57. From the terminal 59 power is applied through a radio frequency choke 61 to a terminal 62. The emitter of a transistor 63 is connected to the terminal 62 and the collector of the transistor 63 is connected to the positive bus 57. A voltage divider consisting of three series resistors 64, 65 and 66 is connected between the terminal 62 and the bus 57. The resistor 64 is connected between the base of the transistor 63 and the terminal 62. The resistor 65 is connected from the base of the transistor 63 to a junction 67 and the resistor 66 is from the junction 67 to the positive bus 57. A Zener diode 68 is connected from the junction 67 to the negative terminal 59 for regulating the base voltage bias on the transistor 63 for line voltage fluctuations. A capacitor 69 is connected in parallel with the resistor 64 between the terminal 62 and the base of the transistor 63 to provide a low impedance path for radio frequency current. The base of the transistor 63 is also connected to a junction 70 through a tuned series LC circuit consisting of an inductor 71 and a capacitor 72. Finally, a capacitor 73 is connected from the terminal 62 to the junction 70. The oscillator circuit, as described above, oscillates at a frequency determined primarily by the resonant frequency of the inductor 71 and the capacitor 72. However, the frequency will be modified somewhat due to loading at the junction 70. The output from the oscillator circuit 56, as taken from the junction 70, is applied through an adjustable inductor 74 to the shielded wire 26 in the coaxial cable 12. At the ultrasonic nebulizer 13, as shown in FIGS. 1 and 2, the center or shielded conductor 26 in the coaxial cable 12 is connected through the thermal switch 21 to the transducer 17 and the shielding on the coaxial cable 12 is also connected to the transducer 17.

Turning for a moment to FIG. 4, an equivalent circuit is shown for a piezoelectric ceramic transducer when driven at or near resonance. A bulk capacitance 80 appears between a pair of electrodes 81 and 82 for the transducer 17. The value of the bulk capacitance 80 is determined to a major extent by the size, shape and spacing between electrodes which connect the terminals 81 and 82 to the ceramic material forming the piezoelectric transducer 17 and to the dielectric properties of the ceramic material. A series RLC circuit is connected in parallel with the bulk capacitance 80. The series circuit includes a resistance 83 which represents mechanical loading on the piezoelectric ceramic transducer 17, an inductance 84, a capacitance 85 and a resistance 86 which represents losses within the transducer 17. The value of the inductance 84 and the capacitance 85 determines the resonant point of the transducer 17. In a typical transducer 17, the resistance 83 will have a value on the order of 40 ohms when power is applied to the transducer 17 and liquid is covering the transducer surface 29 (shown in FIG. 2). However, when liquid is removed from the transducer surface 29, the value of the resistance 83 drops to near zero. The resistance 86 which represents internal losses within the transducer 17 typically has a value of about 2 ohms for a properly designed transducer. As a consequence, when the transducer 17 is operated at or near resonance, the impedance between the electrodes 81 and 82 appears as a capacitance determined by the bulk capacitance 80 shunted by a relatively high load resistance 83 when a liquid load is present on the transducer 17. When the liquid load is removed from the transducer 17, the bulk capacitance 80 is shunted by the low value resistance 86 which represents losses within the transducer 17. This is due to the fact that the resistance 83 decreases from a relatively large value to substantially zero and the series resonant circuit consisting of the inductance 84 and the capacitance 85 represents a low value impedance to radio frequency current at or near the resonant frequency.

Turning again to FIG. 3, the output from the oscillator 56 is tuned to or near the resonant frequency of the transducer 17. This is accomplished by placing liquid within the ultrasonic nebulizer 13 to cover the transducer surface 29. The oscillator 56 is then energized by closing the switch 14 and the variable inductance 71 is adjusted for the best aerosol output from the ultrasonic nebulizer 13. The resulting frequency of the oscillator 56 will be at or near the resonant frequency for the transducer 17. Liquid is then removed from the ultrasonic nebulizer 13 to mechanically unload the transducer 17. While the transducer is in the mechanically unloaded state, the variable inductor 75 which couples the oscillator output to the transducer is adjusted for a minimum current flow to the transducer 17 consistent with maintaining the required aerosol production when liquid is present. At this setting, the inductor 74, the transducer bulk capacitance 80 and any stray capacitance such as the capacitance of the coaxial cable 12 are tuned at or near the resonant frequency of the transducer 17. Since the value of the variable inductor 74 and the loading and unloading of the transducer 17 will have a small effect on the frequency of the output from the oscillator 56, minor adjustments between the inductors 71 and 74 may be required to achieve a balance between the best aerosol generation rate and the best electrical unloading of the transducer 17.

During operation of the apparatus 10, a patient pours a measured dose of medicament through the aerosol outlet 16 into the ultrasonic nebulizer 13. The body of liquid medicament 43 (FIG. 2) will be located over the transducer surface 29 as long as the ultrasonic nebulizer 13 is held in an upright position. The switch 14 is turned to an on position and aerosol is immediately generated within the nebulizer 13. However, the aerosol is retained within the nebulizer 13 by the tubular sleeve 36 which extends downwardly past the aerosol outlet 16. Each time the patient positions his mouth over the aerosol outlet 16 and inhales, he immediately receives aerosol. The patient repeatedly inhales from the aerosol outlet 16 until the entire measured dose of medicament is consumed. At this point, radio frequency power delivered to the ultrasonic nebulizer 13 decreases considerably due to the change in the impedance in the piezoelectric ceramic transducer 17. The power decrease is due to a substantial reduction in the voltage developed across the reactance of the transducer 17 because of the effect of the low resistance value which shunts the bulk capacitance of the transducer. The reduced power delivered to the transducer in the low impedance state protects the transducer 17. It should be noted that the bulk capacitance 80 of the transducer 17 can be minimized through proper designing of the size, shape and spacing of the electrodes 81 and 82. When the bulk capacitance 80 is reduced, the value of the inductor 74 is increased. This in turn increases the current reduction to the mechanically unloaded transducer 17.

Although the present invention has been described above as being embodied within an ultrasonic nebulizer for generating a medicament aerosol, other applications of the invention will also be apparent to those skilled in the ultrasonic art.

What we claim is:

1. An ultrasonic nebulizer comprising, in combination, means defining a liquid reservoir, transducer means for atomizing liquid in the reservoir, said transducer means functioning essentially as a bulk capacitance in parallel with a series resonant circuit when excited within a predetermined frequency range of resonance, said series resonant circuit when excited within such frequency range having a predetermined high resistance when liquid is present in said reservoir and a predetermined lower resistance when mechanically unloaded by the absence of liquid from said reservoir, an oscillator having an output within such frequency range, and means coupling said oscillator output to said transducer means including an inductor, said inductor cooperating with said bulk capacitance and any stray capacitance in circuit with said bulk capacitance to form a series resonant circuit resonating within such frequency range whereby, when liquid is removed from said reservoir, said predetermined low resistance reduces the voltage across said bulk capacitance to in turn reduce power dissipated in such mechanically unloaded transducer means.

2. An ultrasonic nebulizer, as set forth in claim 1, and including means for adjusting the output frequency of said oscillator within such frequency range to achieve a desired liquid atomization level, and wherein said inductor includes inductance adjustment means for minimizing current through said transducer means when said transducer means is excited by said oscillator while liquid is absent from said reservoir.

3. An ultrasonic nebulizer, as set forth in claim 2, and further including switch means responsive to the temperature of said trnsducer means for disconnecting said coupling means from said transducer means when said transducer means exceeds a predetermined high temperature.

4. In an ultrasonic device having a piezoelectric transducer which, when excited within a predetermined frequency range of the transducer resonant frequency, functions essentially as a bulk capacitance in parallel with a series resonant circuit with said series resonant circuit having a predetermined high resistance when said transducer is mechanically loaded and a predetermined lower resistance when said transducer is mechanically unloaded, an improved protective circuit for exciting said transducer comprising, in combination, means for generating an alternating current signal within such predetermined frequency range, and means coupling such alternating current signal to said transducer including an inductor, said inductor, said transducer bulk capacitance and any stray capacitance in circuit with said bulk capacitance resonating within such frequency range whereby, when said transducer is mechanically unloaded, said predetermined low resistance reduces the voltage across the bulk capacitance to in turn reduce power dissipated in such mechanically unloaded transducer.

5. The device of claim 4, further including switch means responsive to the temperature of said transducer for disconnecting said coupling means from said transducer when said transducer exceeds a predetermined high temperature.

6. The device of claim 4, further including means for adjusting the frequency of such alternating current signal within such predetermined frequency range to adjust the output from said transducer, and means for adjusting the inductance of said inductor for minimizing current through said transducer when said transducer is mechanically unloaded.

7. In an ultrasonic device having a piezoelectric transducer which, when excited within a predetermined frequency range of the transducer resonant frequency, has a first impedance when mechanically loaded and a signficantly different second impedance when mechanically unloaded, an improved protective circuit for exciting said transducer comprising, in combination, means for continuously generating an alternating current signal within such predetermined frequency range, and means coupling such alternating current signal to said transducer, said generating means and said coupling means including means for delivering a normal operating power to said transducer when said transducer has such first impedance and for delivering a substantially reduced power to said transducer when said transducer has such second impedance whereby said transducer is protected from damage when mechanically unloaded.

* * * * *